(12) United States Patent
Van Gemert

(10) Patent No.: US 7,584,630 B2
(45) Date of Patent: *Sep. 8, 2009

(54) PHOTOCHROMIC OCULAR DEVICES

(75) Inventor: Barry Van Gemert, Pitcairn, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 629 days.

This patent is subject to a terminal disclaimer.

(21) Appl. No.: 11/196,197

(22) Filed: Aug. 3, 2005

(65) Prior Publication Data

US 2007/0113587 A1    May 24, 2007

Related U.S. Application Data

(63) Continuation-in-part of application No. 10/393,178, filed on Mar. 20, 2003, now abandoned.

(51) Int. Cl.
*C03C 15/00* (2006.01)

(52) U.S. Cl. .................. 65/30.11; 252/586; 351/41; 424/427; 424/428; 424/429; 524/110; 549/389

(58) Field of Classification Search ................. 252/586; 65/30.11; 351/41; 424/427, 428, 429; 524/110; 549/389

See application file for complete search history.

(56) References Cited

U.S. PATENT DOCUMENTS

| | | |
|---|---|---|
| 3,361,706 A | 1/1968 | Meriwether et al |
| 4,166,043 A | 8/1979 | Uhlmann et al. |
| 4,367,170 A | 1/1983 | Uhlmann et al. |
| 4,466,398 A | 8/1984 | Nakanishi et al. |
| 4,495,313 A | 1/1985 | Larsen |
| 4,680,336 A | 7/1987 | Larsen et al. |
| 4,720,356 A | 1/1988 | Chu |
| 4,931,220 A | 6/1990 | Haynes et al. |
| 5,166,345 A | 11/1992 | Akashi |
| 5,236,958 A | 8/1993 | Miyashita |
| 5,252,742 A | 10/1993 | Miyashita |
| 5,260,000 A | 11/1993 | Nandu et al. |
| 5,330,686 A | 7/1994 | Smith et al. |
| 5,359,085 A | 10/1994 | Iwamoto et al. |
| 5,391,327 A | 2/1995 | Ligas et al. |
| 5,458,814 A | 10/1995 | Kumar et al. |
| 5,488,119 A | 1/1996 | Reimann et al. |
| 5,573,712 A | 11/1996 | Kumar et al. |
| 5,578,252 A | 11/1996 | Van Gemert et al. |
| 5,637,726 A | 6/1997 | Collins et al. |
| 5,645,767 A | 7/1997 | Van Gemert |
| 5,650,098 A | 7/1997 | Kumar et al. |
| 5,651,923 A | 7/1997 | Kumar et al. |
| 5,658,501 A | 8/1997 | Kumar et al. |
| 5,753,146 A | 5/1998 | Van Gemert et al. |
| 5,770,115 A | 6/1998 | Misura |
| 5,821,287 A | 10/1998 | Hu et al. |
| 5,965,631 A | 10/1999 | Nicolson et al. |
| 6,020,445 A * | 2/2000 | Vanderlaan et al. ......... 526/279 |
| 6,113,814 A | 9/2000 | Van Gemert et al. |
| 6,123,928 A * | 9/2000 | Sovak et al. ................... 424/59 |
| 6,146,554 A * | 11/2000 | Melzig et al. ............... 252/586 |
| 6,150,430 A | 11/2000 | Walters et al. |
| 6,153,126 A | 11/2000 | Kumar |
| 6,187,444 B1 | 2/2001 | Bowles, III et al. |
| 6,224,945 B1 | 5/2001 | Calderara |
| 6,244,707 B1 | 6/2001 | Faubl |
| 6,296,785 B1 | 10/2001 | Nelson et al. |
| 6,348,604 B1 | 2/2002 | Nelson et al. |
| 6,353,102 B1 | 3/2002 | Kumar |
| 6,555,028 B2 | 4/2003 | Walters et al. |
| 7,320,826 B2 * | 1/2008 | Kumar et al. ............. 428/411.1 |
| 2004/0186241 A1 * | 9/2004 | Gemert .................... 525/329.7 |

FOREIGN PATENT DOCUMENTS

| | | |
|---|---|---|
| WO | WO 97/05213 | 2/1997 |
| WO | WO 01/70719 A2 | 9/2001 |

OTHER PUBLICATIONS

Walters, et al, U.S. Appl. No. 09/828,260, entitled "Polymeric Matrix Compatibilized Naphthopyrans," filed Apr. 6, 2001.
Walters, et al., U.S. Appl. No. 10/393,177, entitled "Indeno-Fused Photochromic Naphthopyrans, Naphthols And Photochromic Articles," filed on Mar. 30, 2003.
*Techniques In Chemistry*, vol. III, "Photochromism", Chapter 3 Title Page and Table of Contents, Glenn H. Brown; John and Wiley & Sons, N.Y., 1971.
Kirk-Othmer Encyclopedia of Chemical Technology, Fourth Edition, 1992, vol. 4, pp. 911-948.
Kirk-Othmer Encyclopedia of Chemical Technology, Fourth Edition, 1993, vol. 6, pp. 669-760.
Kirk-Othmer Encyclopedia of Chemical Technology, Fourth Edition, 1993, vol. 6, pp. 322-325.
Novel Naphthopyran Compounds, Photoresponsive Compositions and Lenses, Frank J. Hughes et al., United States Patent Application No. 2002/0080451 A1, Jun. 27, 2002.
Steffen Jockusch, Nicholas J. Turro, and Forrest R. Blackburn, "Photochromism of 2H-Napththo[1,2-b]pyrans: A Spectroscopic Investigation", J. Phys. Chem A 2002, 106, Jul. 30, 2002, pp. 9236-9241.

* cited by examiner

*Primary Examiner*—Harold Y Pyon
*Assistant Examiner*—Bijan Ahvazi
(74) *Attorney, Agent, or Firm*—Linda Pingitore; Frank P. Mallak; Deborah M. Altman

(57) ABSTRACT

Described are photochromic ocular devices such as contact lenses and intraocular lenses made of an organic polymeric material and at least one photochromic material capable upon exposure to actinic radiation to change from a less ultraviolet radiation absorbing unactivated form to a more ultraviolet radiation absorbing activated form. The photochromic ocular device is capable upon exposure to actinic radiation to exhibit a ratio of greater than 0.5:1.0 of increased ultraviolet radiation absorbance to increased visible radiation absorbance as measured in the Ultraviolet Photochromic Performance Test described herein.

20 Claims, 2 Drawing Sheets

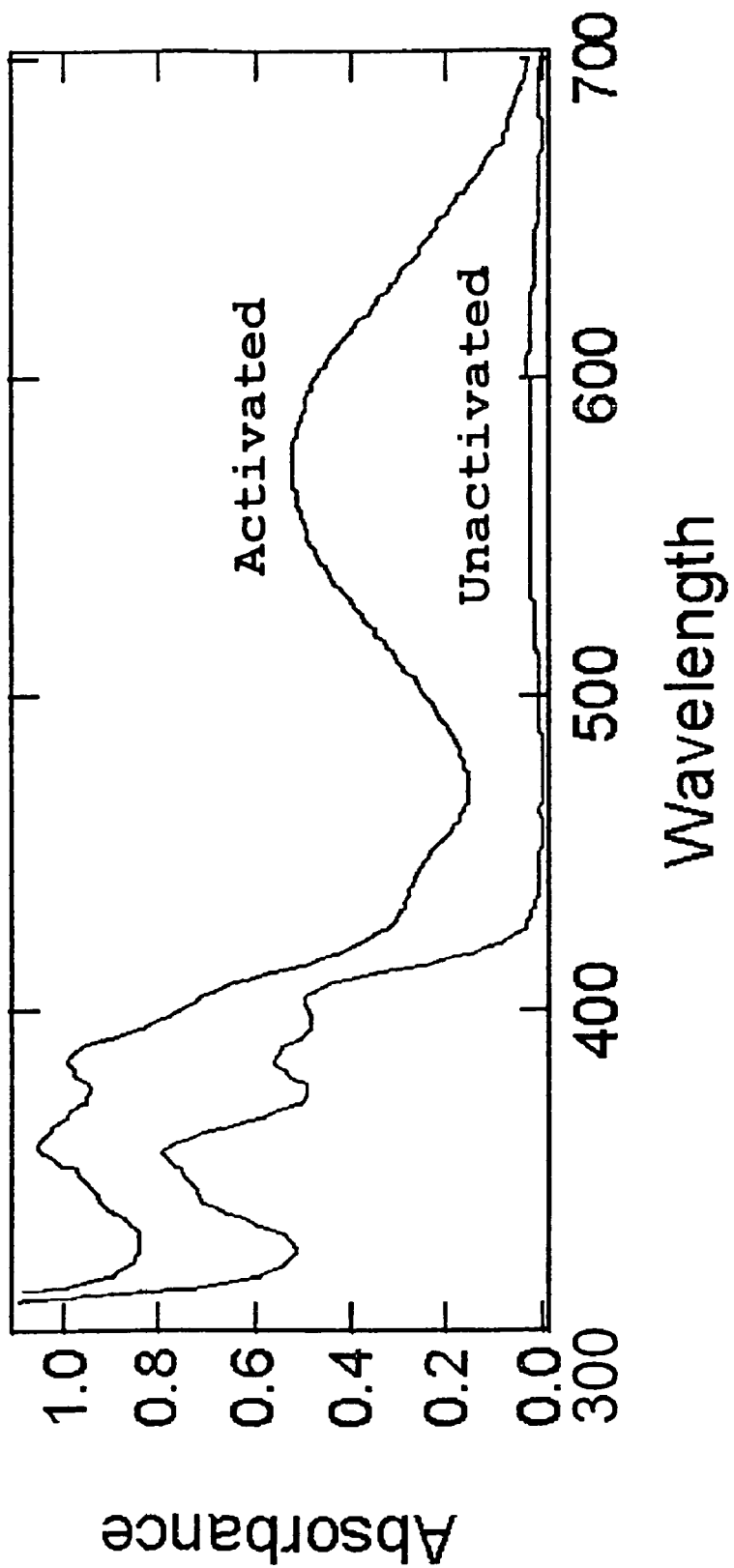
Figure 1. Absorption Spectrum of the Example

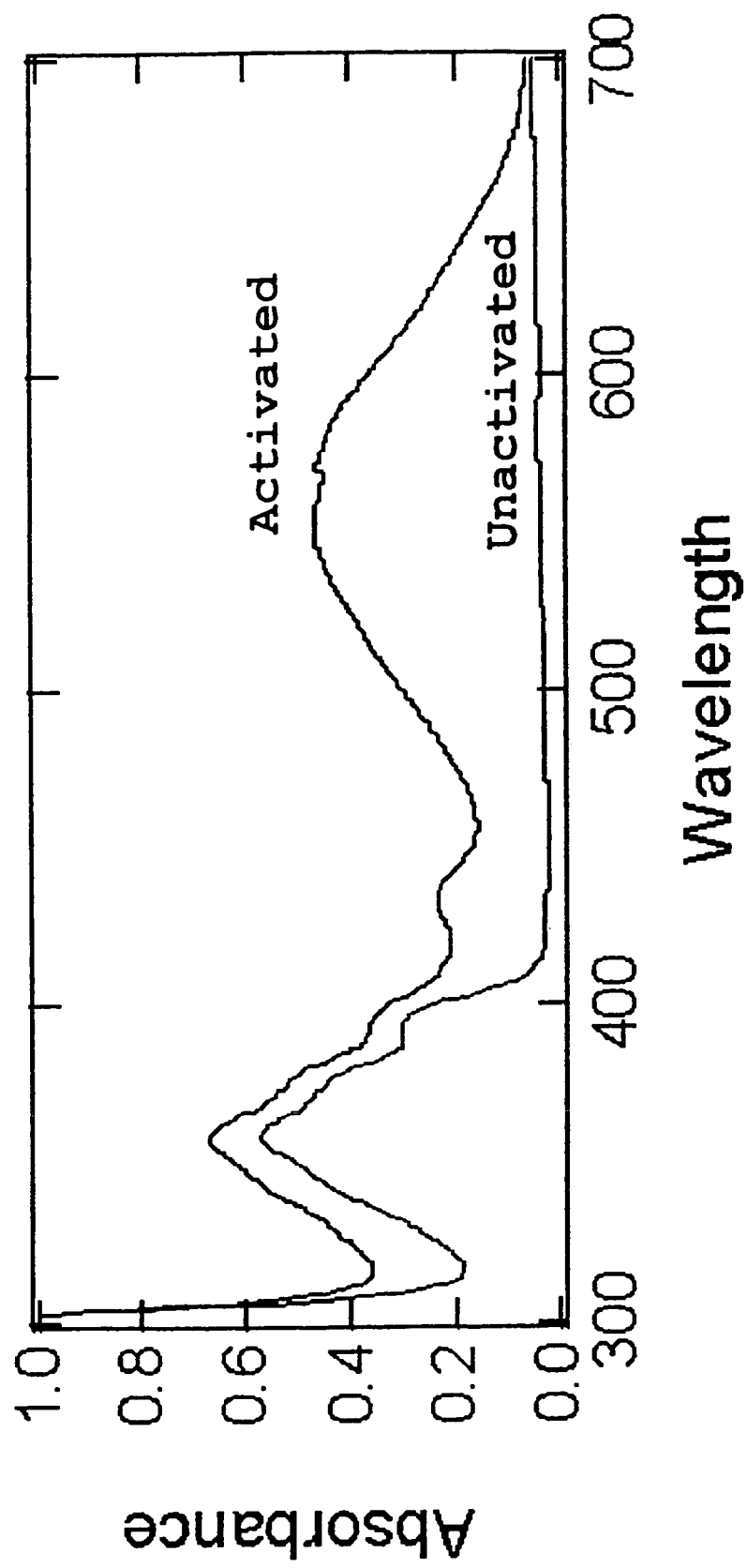
Figure 2. Absorption Spectrum of the Comparative Example

PHOTOCHROMIC OCULAR DEVICES

CROSS-REFERENCE TO RELATED APPLICATION

This application is a continuation-in-part of U.S. patent application Ser. No. 10/393,178, filed on Mar. 20, 2003 now abandoned.

FIELD OF THE INVENTION

The present invention relates to novel ultraviolet radiation absorbing ocular devices. In particular, this invention relates to ocular devices containing photochromic materials that demonstrate an increased UV absorbance upon exposure to ultraviolet radiation present in unfiltered sunlight.

BACKGROUND OF THE INVENTION

Currently, commercially available contact lenses containing ultraviolet radiation absorbing materials are limited in their ability to block ultraviolet radiation from entering the eye. Further, such contact lenses do not meet American National Standards Institute (ANSI Z80.20-1998) Class 1 specifications for ultraviolet radiation absorption. The ANSI specifications require an average percent transmittance of less than 1 percent at 280 to 315 nanometers (nm) and less than 10 percent at 316 to 380 nm.

In one class of contact lenses, described as hydrogels, it has been difficult to incorporate ultraviolet radiation absorbing materials into these lenses because of their hydrophilic nature and expanded structure. The majority of ultraviolet radiation absorbing materials described in the art are generally hydrophobic and have limited solubility in hydrogels. Further, if the aforementioned ultraviolet radiation absorbing materials are added in excess to the ocular device, the properties, e.g., durability, flexibility, hydrophilicity, stability to sterilizing regimes, etc., of the ocular device can be adversely effected.

Therefore, a need remains for an ocular device that provides not only variable protection to visible light but also protection against ultraviolet radiation.

SUMMARY OF THE INVENTION

In accordance with the present invention, a photochromic ocular device is provided comprising:

(a) an organic polymeric material; and (b) at least one photochromic material of Structure I or II below, able to change from a less radiation absorbing unactivated form to a more radiation absorbing activated form upon exposure to actinic radiation. The photochromic ocular device is selected from contact lenses and intraocular devices and is able, upon exposure to actinic radiation, to exhibit a ratio of greater than 0.5:1.0 of increased ultraviolet radiation absorbance to increased visible radiation absorbance as measured in the Ultraviolet Photochromic Performance Test described below.

BRIEF DESCRIPTION OF THE FIGURES

FIG. 1 shows the absorption spectrum from 300 to 700 nanometers (nm) of the Example and FIG. 2 shows the absorption spectrum of the Comparative Example.

DETAILED DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The various embodiments and examples of the present invention as presented herein are understood to be non-limiting with respect to the scope of the invention.

The phrases "at least partially curing a polymerizable composition" or "an at least partially cured polymerizable composition" refer to a polymerizable composition in which the curable or cross-linkable components are from at least partially to fully cured, crosslinked and/or reacted. The degree of cured, crosslinked or reacted components can vary widely, e.g., from 5% to 100% of all of the possible curable, crosslinkable and/or reactable components. The term "ocular device" is defined herein to mean an ophthalmic device that physically resides in or on the eye. Devices can be corrective or non-corrective such as for cosmetic enhancement and include contact lenses and intraocular lenses.

Upon exposure to ultraviolet radiation, the photochromic materials described herein develop an absorbance within the ultraviolet region as well as developing an absorbance within the visible portion of the spectrum.

In one embodiment, the photochromic ocular device or article of the present invention comprises:

(a) an organic polymeric material; and (b) at least one photochromic material of Structure I or II, able to change from a less radiation absorbing unactivated form to a more radiation absorbing activated form upon exposure to actinic radiation; the photochromic ocular device able upon exposure to actinic radiation to exhibit a ratio of greater than 0.5:1.0 of increased ultraviolet radiation absorbance to increased visible radiation absorbance as measured in the Ultraviolet Photochromic Performance Test described in the Example herein. In another embodiment, the photochromic ocular device exhibits a ratio of at least 1.0:1.0. The ratio exhibited by the ocular device of the present invention is at least greater than 0.5:1.0 and may be any higher value, e.g., 0.8, 2, 5, 10 or 100:1.0, inclusive of the aforementioned values, e.g., 0.6:1.0 or 99:1.0.

The ratio is calculated as the greatest difference between the absorbance in the unactivated and activated states in the ultraviolet spectrum (300 to 400 nm) divided by the greatest difference between the absorbance in the unactivated and activated states in the visible spectrum (400 to 700 nm) as measured in the Ultraviolet Photochromic Performance Test. The ratio is determined by plotting the spectrum of the unactivated and activated states over the wavelength range of 300 to 700 nm, measuring the greatest difference between the unactivated and activated states in both the ultraviolet and visible spectrums at the wavelengths of maximum difference and dividing the difference obtained for the ultraviolet spectrum by the difference obtained for the visible spectrum. Each of the greatest differences in the ultraviolet spectrum and visible spectrum can be determined by measuring the difference in millimeters on the plot or by the arithmetic difference in the absorbance units, although the latter method is generally an approximation.

The photochromic material of (b) may be represented by Structure I or II below. In the definitions of the substituents shown in formulae I and II, like symbols have the same meaning unless stated otherwise.

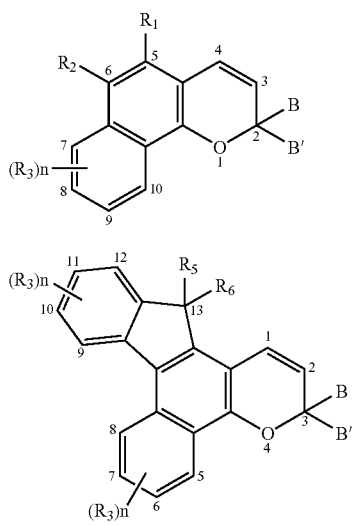

In Structures I and II, $R_1$, $R_2$, $R_5$ and $R_6$ can be the group R. Each $R_3$ can independently be any of the groups of formulae IVA, IVE, and IVF below. The R group can be represented by the following formulae IVA to IVF:

—A     (formula IVA);

—D—A     (formula IVB);

—D—E—U     (formula IVC);

—D—U     (formula IVD);

—E—U     (formula IVE); or

—U     (formula IVF);

wherein —A is represented by the following formula III:

—[(OC$_2$H$_4$)$_x$—(OC$_3$H$_6$)$_y$—(OC$_4$H$_8$)$_z$]—J wherein —J may be: hydroxy, (meth)acryloxy, e.g., acryloxy and methacryloxy, 2-(methacryloxy)ethylcarbamyl, epoxy, $C_1$-$C_6$ alkyl, —OCH$_2$COOH; —OCH(CH$_3$)COOH; —OC(O)(CH$_2$)$_w$COOH; —OC$_6$H$_4$SO$_3$H; —OC$_5$H$_{10}$SO$_3$H; —OC$_4$H$_8$SO$_3$H; —OC$_3$H$_6$SO$_3$H; —OC$_2$H$_4$SO$_3$H; or —OSO$_3$H; w is an integer from 1 to 18; x, y and z are each a number between 0 and 50, and the sum of x, y and z is between 1 and 50; —D— is —C(O)— or —CH$_2$—; —E— is represented by the following formula:

—[(OC$_2$H$_4$)$_x$—(OC$_3$H$_6$)$_y$—(OC$_4$H$_8$)$_z$]— wherein x, y and z are the same as defined for —A; —U is a residue of an organic polyol, having at least one hydroxyl group or a derivative of the residue wherein at least one hydroxyl group has been reacted to form the group J. An organic polyol residue is the remainder of the polyol after at least one hydroxyl group has been reacted.

The group, —U, is a residue of an organic polyol which is defined herein to include hydroxylated carbohydrates discussed below. The residue may be formed by the reaction of one of the hydroxyl groups on the polyol with a precursor of group —D—, such as a carboxylic acid or a methylene halide, a precursor of group —E—, such as polyalkylene glycol or a hydroxyl group as substituent $R_1$, $R_2$, $R_5$ or $R_6$ on the photochromic material (b) represented by Structure I or II. The organic polyol can be represented by G(OH)$_a$ and the residue —U can be represented by the formula —O—G(OH)$_{a-1}$, wherein G is the backbone or main chain of the polyhydroxylated compound and a is at least 2, provided that —U is not the same as —A when —J is hydroxy (see below).

All, none or at least one of the hydroxyls of group —U can be reacted to form a group represented by —J, such as a polymerizable group selected from (meth)acryloxy, 2-(methacryloxy)ethylcarbamyl, epoxy and mixtures thereof. The hydroxyl groups of —U can be reacted to form the carboxyl group containing substituent —J by methods known in the art, e.g., by Reactions B and D in allowed application Ser. No. 09/828,260 filed Apr. 6, 2001, to produce a carboxylated organic polyol residue. The organic polyol residue —U having the sulfo or sulfono terminating groups of —J on it can be produced by acidic condensation of the hydroxyl groups of —U with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. The polymerizable groups, (meth)acryloxy, 2-(methacryloxy) ethylcarbamyl or epoxy, can be added to the polyol residue —U by condensation of the polyol with (meth)acryloyl chloride, isocyanatoethyl methacrylate or epichlorohydrin, respectively.

Non-limiting examples of organic polyols that can be used to form the residue —U in the R group substituent of photochromic material (b) include polyols having at least 2 hydroxy groups such as (a) low molecular weight polyols, e.g., polyols having a molecular weight, i.e., the sum of the atomic weights of the constituent atoms of the polyol, that is less than 500 grams per mole, e.g., aliphatic triols, such as $C_2$-$C_{10}$ aliphatic triols, polyhydric alcohols and alkoxylated low molecular weight polyols; (b) polyester polyols; (c) polyether polyols; (d) amide-containing polyols; (e) epoxy polyols; (f) polyhydric polyvinyl alcohols; (g) urethane polyols; (h) polyacrylic polyols; (i) polycarbonate polyols; and (j) mixtures of such polyols. Such polyols are known to those skilled in the art and are described in U.S. Pat. No. 6,187,444B1.

Non-limiting examples of polyhydroxylated carbohydrates that can be used in the R group substituent of photochromic material (b) include: low molecular weight carbohydrates of the formula $C_e(H_2O)_e$ wherein e is from 3 to 5, e.g., aldotriose, aldoketose, erythrose, ribose, etc.; monosaccharides, e.g., simple sugars such as glucose and fructose; oligosaccharides, i.e., carbohydrates containing from two to ten monosaccharides linked together, e.g., sucrose and cyclodextrins; polysaccharides, i.e., carbohydrates containing more than ten monosaccharides linked together by glycosidic bonds, e.g., starch, cellulose, glycogen, pectin, agar, carrageenan and natural gums such as arabic and tragacanth.

Suitable polyhydroxylated carbohydrates described herein also include glycosides which are mono- and oligosaccharides linked to nonsugar organic compounds. An example is the product of the reaction of D-glucose with ethanol to form ethyl α- & β-D-glucopyranosides. Another class of polyhydroxylated carbohydrates are the glycoconjugates composed of glycoproteins, proteoglycans, peptidoglycans and glycolipids. Still another class of carbohydrates includes various reaction products such as the sugar alcohols, e.g., xylitol and glucitol, produced by the reduction of mono- and oligosaccharides. Further examples of reaction products include low molecular weight carbohydrates, mono- and oligosaccharides in which one or more of the hydroxyl groups has been oxidized to a carboxylic acid functional group, or replaced by an amino group, thiol group or a halogen atom. Further information about carbohydrates that can be suitable for use in the R— group is found in the *Kirk-Othmer Encyclopedia of Chemical Technology*, Fourth Edition, 1992, Volume 4, pages 911-948.

The —U group may alternatively be a residue of polyols selected from low molecular weight polyols and extended polyols. Examples of such polyols include (a) glycerol, pentaerythritol and trimethylolpropane, (b) ethoxylated glycerol, ethoxylated pentaerythritol and ethoxylated trimethylolpropane; and (c) polyols (a) and (b) having at least 1 hydroxyl group reacted to produce substituent —J, a polymerizable group selected from (meth)acryloxy, 2-(methacryloxy)ethylcarbamyl or epoxy, and a mixture thereof.

The group, $—(OC_2H_4)_x—$, represents poly(ethylene oxide); $—(OC_3H_6)_y—$, represents poly(propylene oxide); and, $—(OC_4H_8)_z—$, represents poly(butylene oxide). When used in combination, the poly(ethylene oxide), poly(propylene oxide) and poly(butylene oxide) groups of R can be in a random or block order within the R moiety. The letters x, y and z are each a number between 0 and 50 and the sum of x, y and z is between 1 and 50. The sum of x, y and z can be any number that falls within the range of 1 to 50, e.g., 1, 2, 3 . . . 50. The sum can also range from any lower number to any higher number within the range of 1 to 50, e.g., 6 to 50, 31 to 50. The numbers for x, y, and z are average values and can be partial numbers, e.g., 9.5.

In one embodiment, $R_1$ is the group R, $C_1$-$C_3$ alkyl or the group, —C(O)W, W being —$OR_7$, —$N(R_8)R_9$, piperidino or morpholino, wherein $R_7$ is allyl, $C_1$-$C_6$ alkyl, phenyl, mono ($C_1$-$C_6$)alkyl substituted phenyl, mono($C_1$-$C_6$)alkoxy substituted phenyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl or $C_1$-$C_6$ haloalkyl; $R_8$ and $R_9$ are each independently selected from $C_1$-$C_6$ alkyl, $C_5$-$C_7$ cycloalkyl, phenyl, mono-substituted phenyl and di-substituted phenyl, the phenyl substituents being $C_1$-$C_6$ alkyl or $C_1$-$C_6$ alkoxy, and the halo substituent being chloro or fluoro.

$R_2$ may be selected from the group R, mono-R-substituted phenyl, hydrogen, $C_1$-$C_6$ alkyl, $C_3$-$C_7$ cycloalkyl, phenyl, mono-substituted phenyl, di-substituted phenyl, the group —$OR_{10}$ and —$OC(O)R_{10}$, wherein $R_{10}$ is $C_1$-$C_6$ alkyl, phenyl ($C_1$-$C_3$)alkyl, mono($C_1$-$C_6$)alkyl substituted phenyl($C_1$-$C_3$) alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl or mono($C_1$-$C_4$) alkyl substituted $C_3$-$C_7$ cycloalkyl, and the phenyl substituent being $C_1$-$C_6$ alkyl or $C_1$-$C_6$ alkoxy.

At least one $R_3$ in Structure I is attached at position 9. In Structure II, at least one $R_3$ group is attached at each of positions 6 and 11. Each $R_3$ may independently be the group —A, —EU, —U, $C_1$-$C_6$ alkyl, phenyl, mono-substituted phenyl, di-substituted phenyl, the group —$OR_{10}$ or —$OC(O)R_{10}$, wherein $R_{10}$ is $C_1$-$C_6$ alkyl, phenyl($C_1$-$C_3$)-alkyl, mono($C_1$-$C_6$)alkyl substituted phenyl($C_1$-$C_3$)alkyl, mono($C_1$-$C_6$) alkoxy substituted phenyl($C_1$-$C_3$)alkyl, $C_1$-$C_6$ alkoxy($C_2$-$C_4$) alkyl, $C_3$-$C_7$ cycloalkyl or mono($C_1$-$C_4$)alkyl substituted $C_3$-$C_7$ cycloalkyl, the phenyl substituent being $C_1$-$C_6$ alkyl or $C_1$-$C_6$ alkoxy. Alternatively, each $R_3$ is independently a nitrogen-containing group selected from:

(i) —$N(R_{11})R_{12}$ wherein $R_{11}$ and $R_{12}$ are each independently selected from hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl and fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein the aryl group is phenyl or naphthyl or $R_{11}$ and $R_{12}$ come together with the nitrogen atom to form a $C_3$-$C_{20}$ hetero-bicycloalkyl ring or a $C_4$-$C_{20}$ hetero-tricycloalkyl ring;

(ii) a nitrogen containing ring represented by the following graphic formula VA:

VA wherein each Y is independently selected for each occurrence from —$CH_2$—, —$CH(R_{13})$—, —$C(R_{13})(R_{13})$—, —$CH$ (aryl)-, —$C(aryl)_2$—, and —$C(R_{13})(aryl)$-, and X is selected from —Y—, —O—, —S—, —S(O)—, —$S(O_2)$—, —NH—, —$N(R_{13})$— and —N(aryl)-, wherein $R_{13}$ is $C_1$-$C_6$ alkyl, the aryl is phenyl or naphthyl, m is the integer 1, 2 or 3, and p is the integer 0, 1, 2, or 3 and when p is O, X is Y;

(iii) a group represented by one of the following graphic formulae VB and VC:

VB

VC wherein $R_{15}$, $R_{16}$ and $R_{17}$ are each independently selected for each occurrence in each formula from hydrogen, $C_1$-$C_6$ alkyl, phenyl and naphthyl, or the groups $R_{15}$ and $R_{16}$ together form a ring of 5 to 8 carbon atoms and each $R_{14}$ is independently selected for each occurrence in each formula from $C_1$-$C_6$ alkyl, $C_1$-$C_6$ alkoxy, fluoro and chloro and p is the same as defined herein before;

(iv) unsubstituted, mono- or di-substituted $C_4$-$C_{18}$ spirobicyclic amine; and (v) unsubstituted, mono- or di-substituted $C_4$-$C_{18}$ spirotricyclic amine; the substituents for (iv) and (v) are independently selected for each occurrence from aryl, $C_1$-$C_6$ alkyl, $C_1$-$C_6$ alkoxy and phenyl($C_1$-$C_6$)alkyl and n is selected from the integers 0, 1 and 2.

$R_5$ and $R_6$ may together form an oxo group, a spiro-carbocyclic ring containing 3 to 6 carbon atoms or a spiro-heterocyclic group containing 1 or 2 oxygen atoms and 3 to 6 carbon atoms including the spirocarbon atom, the spiro-carbocyclic and spiro-heterocyclic groups being annellated with 0, 1 or 2 benzene rings. Examples of the spiro-carbocyclic ring substituents include spirofluoreno, spirocyclopropyl, spirocyclobutyl, spirocyclopentyl, spirocyclohexyl, spiroindan-1-yl, spiroindan-2-yl, etc. Examples of the spiroheterocyclic group include spiroxantheno and compounds which can be represented by the expression: (-0-($C_2$-$C_5$ alkanediyl)-0-), e.g., spiro-1,3-dioxolane-2, spiro-1,3-dioxane-2, etc., or spirolactones, such as butyrolactone, propiolactone, etc.

In an alternate embodiment, $R_5$ and $R_6$ are each independently the group R, hydrogen, $C_1$-$C_6$ alkyl, $C_3$-$C_7$ cycloalkyl, allyl, phenyl, mono-substituted phenyl, benzyl, mono-substituted benzyl, chloro, fluoro, the group, —C(O)X', wherein X' is hydroxy, $C_1$-$C_6$ alkyl, $C_1$-$C_6$ alkoxy, phenyl, mono-substituted phenyl, amino, mono($C_1$-$C_6$)alkylamino, or di($C_1$-$C_6$) alkylamino; or $R_5$ and $R_6$ are each independently the group, —$OR_{18}$, wherein $R_{18}$ is $C_1$-$C_6$ alkyl, phenyl($C_1$-$C_3$)alkyl, mono($C_1$-$C_6$)alkyl substituted phenyl($C_1$-$C_3$)alkyl, mono ($C_1$-$C_6$)alkoxy substituted phenyl($C_1$-$C_3$)alkyl, $C_1$-$C_6$ alkoxy ($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, the group, —CH($R_{19}$)Y', wherein $R_{19}$ is hydrogen or $C_1$-$C_3$ alkyl and Y' is CN, $CF_3$, or $COOR_{20}$ and $R_{20}$ is hydrogen or $C_1$-$C_3$ alkyl; or $R_{18}$ is the group, —C(O)Z, wherein Z is hydrogen, $C_1$-$C_6$ alkyl, $C_1$-$C_6$ alkoxy, the unsubstituted, mono- or di-substituted aryl groups phenyl or naphthyl, phenoxy, mono- or di-($C_1$-$C_6$)alkyl substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, each of the phenyl, benzyl and aryl group substituents being $C_1$-$C_6$ alkyl or $C_1$-$C_6$ alkoxy.

Group B may typically be an unsubstituted aryl group, phenyl, or naphthyl. The group B' may be:
(i) unsubstituted, mono-, di- or tri-substituted aryl groups, phenyl or naphthyl;
(ii) 9-julolidinyl or the unsubstituted, mono- or di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl or fluorenyl, each of the aryl and heteroaromatic substituents in (i) and (ii) being the group R, hydroxy, aryl, mono(C1-C6)alkoxyaryl, di(C1-C6)alkoxyaryl, mono(C1-C6)alkylaryl, di(C1-C6)alkylaryl, chloroaryl, fluoroaryl, C3-C7 cycloalkylaryl, C3-C7 cycloalkyl, C3-C7 cycloalkyloxy, C3-C7 cycloalkyloxy(C1-C6) alkyl, C3-C7 cycloalkyloxy(C1-C6)alkoxy, aryl(C1-C6)alkyl, aryl(C1-C6)alkoxy, aryloxy, aryloxy(C1-C6) alkyl, aryloxy(C1-C6)alkoxy, mono- or di-(C1-C6) alkylaryl(C1-C6)alkyl, mono- or di-(C1-C6)alkoxyaryl (C1-C6)alkyl, mono- or di-(C1-C6)alkylaryl(C1-C6) alkoxy, mono- or di-(C1-C6)alkoxyaryl(C1-C6)alkoxy, amino, mono(C1-C6)alkylamino, di(C1-C6)alkylamino, diarylamino, N—(C1-C6)alkylpiperazino, N-arylpiperazino, aziridino, indolino, piperidino, arylpiperidino, morpholino, thiomorpholino, tetrahydroquinolino, tetrahydroisoquinolino, pyrryl, C1-C6 alkyl, C1-C6 chloroalkyl, C1-C6 fluoroalkyl, C1-C6 alkoxy, mono(C1-C6)alkoxy(C1-C4)alkyl, acryloxy, methacryloxy, bromo, chloro or fluoro, the aryl being phenyl or naphthyl;
(iii) the unsubstituted or mono-substituted groups pyrazolyl, imidazolyl, pyridyl, pyrazolinyl, imidazolinyl, pyrrolinyl, phenothiazinyl, phenoxazinyl, phenazinyl or acridinyl, each of the substituents being $C_1$-$C_6$ alkyl, $C_1$-$C_4$ alkoxy, phenyl, fluoro, chloro or bromo;
(iv) monosubstituted phenyl, having a substituent at the para position that is a linking group, —(CH2)t- or —O—(CH2)t-, wherein t is the integer 1, 2, 3, 4, 5 or 6, connected to an aryl group, which is a member of another photochromic material, e.g., a naphthopyran;
(v) the group represented by one of the following graphic formulae VIA and VIB:

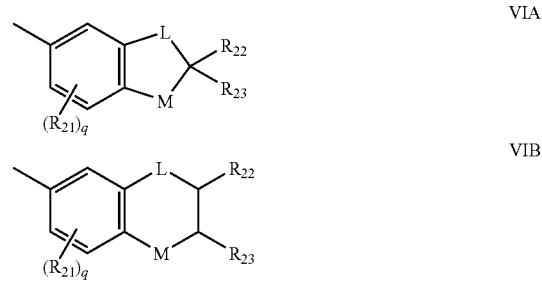

wherein L is carbon or oxygen and M is oxygen or substituted nitrogen, provided that when M is substituted nitrogen, L is carbon, the nitrogen substituents being hydrogen, $C_1$-$C_6$ alkyl and $C_2$-$C_6$ acyl; each $R_{21}$ is $C_1$-$C_6$ alkyl, $C_1$-$C_6$ alkoxy, hydroxy, chloro or fluoro; $R_{22}$ and $R_{23}$ are each hydrogen or $C_1$-$C_6$ alkyl; and q is the integer 0, 1 or 2;
(vi) $C_1$-$C_6$ alkyl, $C_1$-$C_6$ chloroalkyl, $C_1$-$C_6$ fluoroalkyl, $C_1$-$C_6$ alkoxy($C_1$-$C_4$)alkyl, $C_3$-$C_6$ cycloalkyl, mono($C_1$-$C_6$)alkoxy($C_3$-$C_6$)cycloalkyl, mono($C_1$-$C_6$)alkyl($C_3$-$C_6$)-cycloalkyl, chloro($C_3$-$C_6$)cycloalkyl, fluoro($C_3$-$C_6$)cycloalkyl or $C_4$-$C_{12}$ bicycloalkyl; or
(vii) the group represented by the following graphic formula VIC:

wherein P is hydrogen or $C_1$-$C_4$ alkyl and Q is selected from the unsubstituted, mono-, and di-substituted members of the group consisting of naphthyl, phenyl, furanyl and thienyl, each of the group substituents being $C_1$-$C_4$ alkyl, $C_1$-$C_4$ alkoxy, fluoro or chloro.

In one embodiment, there can be 0 or 1 R group or mono-R-substituted phenyl group on the photochromic material. In another embodiment, there is at least one R group or mono-R-substituted phenyl on the photochromic material. For example, the number of R groups (including the mono-R-substituted phenyl) can be 2, 3, 4, 5 or a number equal to the total number of substituents possible on the photochromic material. When there is more than one R group or mono-R-substituted phenyl on the photochromic material, the R groups can be the same or different, e.g., there can be two different groups selected from formulae IVA to IVF.

In a particular embodiment, the photochromic material (b) of the present invention is represented by Structure I or II, the R group is represented by formulae: IVA, IVB, IVE or IVF; $R_1$ is the group R, or $R_1$ is the group, —C(O)W, W being —$OR_7$ or —$N(R_8)R_9$, wherein $R_7$ is $C_1$-$C_4$ alkyl, phenyl, mono($C_2$-$C_4$)alkyl substituted phenyl, mono($C_1$-$C_4$)alkoxy substituted phenyl, phenyl($C_1$-$C_2$)alkyl, mono($C_1$-$C_4$)alkyl substituted phenyl($C_1$-$C_2$)alkyl, mono($C_1$-$C_4$)alkoxy substituted phenyl($C_1$-$C_2$)alkyl, mono($C_1$-$C_4$)alkoxy($C_2$-$C_3$)alkyl or $C_1$-$C_4$ haloalkyl; $R_8$ and $R_9$ are each independently $C_1$-$C_4$ alkyl, $C_5$-$C_7$ cycloalkyl, phenyl, mono- or di-substituted phenyl, the phenyl substituents being $C_1$-$C_4$ alkyl or $C_1$-$C_4$ alkoxy, the halo substituents being chloro or fluoro. In a further embodiment, $R_1$ is the group R or the group, —C(O)W, wherein W is the group, —$OR_7$, and $R_7$ is a $C_1$-$C_3$ alkyl.

In another embodiment, $R_2$ is the group R, mono-R-substituted phenyl, hydrogen, $C_1$-$C_3$ alkyl, $C_3$-$C_5$ cycloalkyl, phenyl, mono- or di-substituted phenyl or the group —$OR_{10}$, wherein $R_{10}$ is $C_1$-$C_4$ alkyl, phenyl($C_1$-$C_2$)alkyl, mono($C_1$-$C_4$)alkyl substituted phenyl($C_1$-$C_2$)alkyl, mono($C_1$-$C_4$)alkoxy substituted phenyl($C_1$-$C_2$)alkyl, $C_1$-$C_4$ alkoxy($C_2$-$C_4$)alkyl, $C_5$-$C_7$ cycloalkyl or mono($C_1$-$C_3$)alkyl substituted $C_5$-$C_7$ cycloalkyl, and the phenyl substituents are $C_1$-$C_3$ alkyl or $C_1$-$C_3$ alkoxy. In a further embodiment, $R_2$ is hydrogen, the group R, mono-R-substituted phenyl, $C_1$-$C_3$ alkyl, phenyl, mono- or di-substituted phenyl or the group —$OR_{10}$, wherein $R_{10}$ is $C_1$-$C_3$ alkyl and the phenyl substituents are methyl or methoxy.

In another embodiment, each $R_3$ is the group —A, —EU, —U, or the group —$OR_{10}$, wherein $R_{10}$ is $C_1$-$C_4$ alkyl, phenyl($C_1$-$C_2$)alkyl, mono($C_1$-$C_4$)alkyl substituted phenyl($C_1$-$C_2$)alkyl, mono($C_1$-$C_4$)alkoxy substituted phenyl($C_1$-$C_2$)alkyl, $C_1$-$C_4$ alkoxy($C_2$-$C_4$)alkyl, $C_5$-$C_7$ cycloalkyl or mono($C_1$-$C_3$)alkyl substituted $C_5$-$C_7$ cycloalkyl, and the phenyl substituents are $C_1$-$C_3$ alkyl or $C_1$-$C_3$ alkoxy.

Alternatively, each $R_3$ is independently a nitrogen-containing group comprising:

(i) —$N(R_{11})R_{12}$, $R_{11}$ and $R_{12}$ each being independently selected from $C_1$-$C_6$ alkyl and phenyl;

(ii) a nitrogen containing ring represented by the graphic formula VA wherein each Y being —$CH_2$— and X being independently selected from —Y—, —O—, —S—, —$N(R_{13})$— and —N(phenyl)-, $R_{13}$ being $C_1$-$C_6$ alkyl, m being selected from the integers 1, 2 and 3, and p being selected from the integers 0, 1, 2 and 3;

(iii) a group represented by one of graphic formulae VB and VC wherein R15, R16 and R17 each being independently selected from hydrogen and C1-C5 alkyl, R14 being independently selected from hydrogen, C1-C4 alkyl, C1-C4 alkoxy, fluoro and chloro;

(iv) unsubstituted or mono-substituted C5-C18 spirobicyclic amine; or (v) unsubstituted or mono-substituted C5-C18 spirotricyclic amine; the substituents for (c)(iv) and (v) are independently selected for each occurrence from phenyl, C1-C6 alkyl and C1-C6 alkoxy and n is the integer 1 or 2.

In another embodiment, $R_5$ and $R_6$ are each selected from the group R, hydrogen, $C_1$-$C_4$ alkyl, $C_3$-$C_6$ cycloalkyl, chloro, fluoro or the group, —$OR_{18}$, wherein $R_{18}$ is $C_1$-$C_3$ alkyl, phenyl($C_1$-$C_2$)alkyl, mono($C_1$-$C_3$)alkyl substituted phenyl($C_1$-$C_3$)alkyl, mono($C_1$-$C_3$)alkoxy substituted phenyl($C_1$-$C_3$)alkyl, $C_1$-$C_3$ alkoxy($C_2$-$C_4$)alkyl, $C_1$-$C_3$ chloroalkyl, $C_1$-$C_3$ fluoroalkyl, or the group, —CH($R_{19}$)Y', wherein $R_{19}$ is hydrogen or $C_1$-$C_2$ alkyl and Y' is CN or $COOR_{20}$, $R_{20}$ being hydrogen or $C_1$-$C_2$ alkyl, or $R_{18}$ is the group, —C(O)Z, wherein Z is hydrogen, $C_1$-$C_3$ alkyl, $C_1$-$C_3$ alkoxy, phenyl, naphthyl, the mono-substituted aryl groups, phenyl or naphthyl, phenoxy, mono- or di-($C_1$-$C_3$)alkyl substituted phenoxy, mono- or di-($C_1$-$C_3$)alkoxy substituted phenoxy, mono($C_1$-$C_3$)alkylamino, phenylamino, mono- or di-($C_1$-$C_3$)alkyl substituted phenylamino, or mono- or di-($C_1$-$C_3$)alkoxy substituted phenylamino, each of the aryl group substituents being independently selected from $C_1$-$C_3$ alkyl and $C_1$-$C_3$ alkoxy.

In a particular embodiment, photochromic material (b) is represented by Structure II. At least one $R_3$ group is attached at each of positions 6 and 11. Each $R_3$ is the group R represented by formula IVA, IVE or IVF, or the group —$OR_{10}$, wherein $R_{10}$ is $C_1$-$C_3$ alkyl; or each $R_3$ is:

(i) —$N(R_{11})R_{12}$, $R_{11}$ and $R_{12}$ each being $C_1$-$C_3$ alkyl;

(ii) a nitrogen containing ring represented by graphic formula VA wherein each Y for each occurrence being —$CH_2$— and X being independently selected from —Y—, —O—, and —$N(R_{13})$—, $R_{13}$ being $C_1$-$C_4$ alkyl, m being selected from the integers 1 and 2, and p being selected from the integers 0, 1 and 2; or (iii) a group represented by graphic formulae VC or VB wherein $R_{15}$, $R_{16}$, and $R_{17}$ each being hydrogen and n is 1 or 2.

Photochromic material (b) is often selected from:

(a) 3-(4-methoxyphenyl)-3-phenyl-6,11-dimethoxy-13-methyl-13-(2-{2-[N-(2-methacryloxyethyl)carbamoyloxy]ethoxy}ethoxy)-3H,13H-indeno[2,'3,'3,4]naphtho[1,2-b]pyran;

(b) 3-(4-methoxyphenyl)-3-phenyl-6,11-dimethoxy-13-methyl-13-(2-(2-(2-methacryloxyethyl)ethoxy)ethoxy)-3H,13H-indeno[2,'3,'3,4]naphtho[1,2-b]pyran;.

(c) 3,3-diphenyl-6,7-dimethoxy-13-methyl-13-(2-(2-(2-methacryloxyethyl)ethoxy)ethoxy)-3H,13H-indeno[2,'3,'3,4]-naphtho[1,2-b]pyran;

(d) 3-(4-methoxyphenyl)-3-(2,4-dimethoxyphenyl-6,11-dimethoxy-13-methyl-13-(2-(2-(2-methacryloxyethyl)ethoxy)ethoxy)-3H,13H-indeno[2,'3,'3,4]naphtho[1,2-b]pyran;

(e) 3-(4-methoxyphenyl)-3-phenyl-6-methoxy-7-morpholino-13-methyl-13-(2-(2-(2-methacryloxyethyl)ethoxy)ethoxy)-3H,13H-indeno[2,'3,'3,4]naphtho[1,2-b]pyran;

(f) 3,3-diphenyl-6,7,10,11-tetramethoxy-13-ethyl-13-(2-{2-[N-(2-methacryloxyethyl)carbamoyloxy]ethoxy}ethoxy)-3H,13H-indeno[2,'3,'3,4]naphtho[1,2-b]pyran;

(g) 2,2-diphenyl-5-(2-(2-(2-methacryloxyethyl)ethoxy)ethoxy)carbonyl-9-methoxy-2H-naphtho[1,2-b]pyran;

(h) 2,2-di(4-fluorophenyl)-5-(2-(2-(2-methacryloxy-ethyl)ethoxy)ethoxy)carbonyl-6-phenyl-9-methoxy-2H-naphtho[1,2-b]pyran;

(i) 2,2-diphenyl-5-(2-(2-(2-methacryloxyethyl)ethoxy)ethoxy)carbonyl-8,9-dimethoxy-2H-naphtho[1,2-b]pyran; and (j) mixtures thereof.

The materials represented by Structures I and II can be produced by methods known to those skilled in the art. For example, the materials represented by Structure I can be produced by methods disclosed in U.S. Pat. No. 5,458,814 at column 2, line 18 to column 9, line 5; U.S. Pat. No. 5,573,712 at column 2, line 19 to column 8, line 64; U.S. Pat. No. 5,650,098 at column 2, line 7 to column 9, line 52; and U.S. Pat. No. 5,651,923 at column 2, line 11 to column 14, line 62; the materials represented by Structure II can be produced by the methods disclosed in U.S. patent application Ser. No. 10/343,177 filed on Mar. 20, 2003; and the materials represented by Structures I and II can be produced by methods described in U.S. Pat. No. 6,113,814 at column 2, line 24 to column 23, line 29 and allowed U.S. patent application Ser. No. 09/828,260 filed Apr. 6, 2001, which disclosures are incorporated herein by reference.

Examples of photochromic materials (b) represented by Structures I and II or a mixture thereof can be used in various ocular devices such as contact lenses that either have or do not have prescribed refractive and/or prismatic powers, haptic (scleral) contact lenses as well as flexible paralimbal contact lenses and intraocular lenses such as intracorneal lenses. Such lenses are described in ANSI Z80.20-1998 American National Standard for Ophthalmics—Contact Lenses—Standard Terminology, Tolerances, Measurements and Physicochemical Properties.

It is contemplated that the photochromic material (b) can be used alone or in combination with other such materials in ocular devices of the present invention, or in combination with one or more other organic photochromic materials (c), e.g., photochromic materials having at least one activated absorption maxima within the range of between about 400 and 700 nanometers.

The optional photochromic material (c) can include the following classes of materials: chromenes, e.g., naphthopyrans, benzopyrans, indenonaphthopyrans, phenanthropyrans or mixtures thereof; spiropyrans, e.g., spiro(benzindoline) naphthopyrans, spiro(indoline)benzopyrans, spiro(indoline) naphthopyrans, spiro(indoline)quinopyrans and spiro(indoline)pyrans; oxazines, e.g., spiro(indoline)naphthoxazines, spiro(indoline)pyridobenzoxazines, spiro(benzindoline)pyridobenzoxazines, spiro(benzindoline)naphthoxazines and spiro(indoline)benzoxazines; mercury dithizonates, fulgides, fulgimides and mixtures of such photochromic compounds.

Such photochromic materials and complementary photochromic materials are described in U.S. Pat. No. 4,931,220 at column 8, line 52 to column 22, line 40; U.S. Pat. No. 5,645,767 at column 1, line 10 to column 12, line 57; U.S. Pat. No. 5,658,501 at column 1, line 64 to column 13, line 17; U.S. Pat. No. 6,153,126 at column 2, line 18 to column 8, line 60; U.S. Pat. No. 6,296,785 at column 2, line 47 to column 31, line 5; U.S. Pat. No. 6,348,604 at column 3, line 26 to column 17, line 15; and U.S. Pat. No. 6,353,102 at column 1, line 62 to column 11, line 64, the disclosures of the aforementioned patents are incorporated herein by reference. Spiro(indoline) pyrans are also described in the text, *Techniques in Chemistry*, Volume III, "Photochromism", Chapter 3, Glenn H. Brown, Editor, John Wiley and Sons, Inc., New York, 1971.

Photochromic material (c) can also comprise polymerizable photochromic materials, such as polymerizable naphthoxazines disclosed in U.S. Pat. No. 5,166,345 at column 3, line 36 to column 14, line 3; polymerizable spirobenzopyrans disclosed in U.S. Pat. No. 5,236,958 at column 1, line 45 to column 6, line 65; polymerizable spirobenzopyrans and spirobenzothiopyrans disclosed in U.S. Pat. No. 5,252,742 at column 1, line 45 to column 6, line 65; polymerizable fulgides disclosed in U.S. Pat. No. 5,359,085 at column 5, line 25 to column 19, line 55; polymerizable naphthacenediones disclosed in U.S. Pat. No. 5,488,119 at column 1, line 29 to column 7, line 65; polymerizable spirooxazines disclosed in U.S. Pat. No. 5,821,287 at column 3, line 5 to column 11, line 39; polymerizable polyalkoxylated naphthopyrans disclosed in U.S. Pat. No. 6,113,814 at column 2, line 23 to column 23, line 29; and the polymerizable photochromic compounds disclosed in WO97/05213 and allowed U.S. application Ser. No. 09/828,260 filed Apr. 6, 2001. The disclosures of the aforementioned patents on polymerizable photochromic materials are incorporated herein by reference.

Other examples of photochromic materials that can be used include organo-metal dithiozonates, e.g., (arylazo)-thioformic arylhydrazidates, e.g., mercury dithizonates which are described in, for example, U.S. Pat. No. 3,361,706 at column 2, line 27 to column 8, line 43; and fulgides and fulgimides, e.g., the 3-furyl and 3-thienyl fulgides and fulgimides, which are described in U.S. Pat. No. 4,931,220 at column 1, line 39 through column 22, line 41, the disclosures of which are incorporated herein by reference.

The optional photochromic material (c) may be a form of organic photochromic material resistant to the effects of a polymerization initiator that can also be used in the photochromic articles of the present invention. Such organic photochromic materials include photochromic compounds in admixture with a resinous material that has been formed into particles and encapsulated in metal oxides, which are described in U.S. Pat. Nos. 4,166,043 and 4,367,170 at column 1 line 36 to column 7, line 12, which disclosure is incorporated herein by reference.

Photochromic material (b) with or without photochromic material (c) can be associated with the organic polymeric material by various methods described in the art. For example, the total amount of photochromic material can be incorporated into the organic polymeric material used to form the photochromic ocular device by various methods such as by adding the photochromic materials to one or more of the materials used to form the organic polymeric material; the photochromic materials can be incorporated into the at least partially cured polymerizate by imbibition, permeation or other transfer methods as known by those skilled in the art; a polymerizable composition containing photochromic materials can be added or injected into a mold and polymerized by what, for example, is commonly referred to in the art as a cast-in-place process. When the polymerizable composition comprises highly reactive materials, e.g., materials used to form polyurethanes, a process such as reaction-injection-molding can be used.

The term "imbibition" or "imbibe" is intended to mean and include permeation of the photochromic materials individually or with other non-photochromic materials into the polymerizate, solvent assisted transfer absorption of the photochromic materials into a polymerizate, vapor phase transfer, and other such transfer mechanisms.

The photochromic materials described herein, e.g., photochromic materials (b) and (c), can be a variety of materials. Examples include, of course, a single photochromic compound, a mixture of photochromic compounds, a material comprising at least one photochromic compound, such as a plastic polymeric resin or an organic monomeric or oligomeric solution, a material such as a monomer or polymer to which at least one photochromic compound is chemically bonded, a material comprising and/or having chemically bonded to it at least one photochromic compound, the outer surface of the material being encapsulated (encapsulation is a form of coating), for example with a polymeric resin or a protective coating such as a metal oxide that prevents contact of the photochromic material with external materials such as oxygen, moisture and/or chemicals that have a negative effect on the photochromic material, such materials can be formed into a particulate prior to applying the protective coating as described in U.S. Pat. Nos. 4,166,043 and 4,367,170, a photochromic polymer, e.g., a photochromic polymer comprising photochromic compounds bonded together or mixtures thereof.

Each of photochromic materials (b) with or without the other photochromic materials (c) described herein can be used in widely varying amounts and ratios. Generally, the photochromic materials are used in such an amount or ratio that an organic polymeric material to which the photochromic materials are associated, exhibits a desired resultant color, e.g., a substantially neutral color when activated with unfiltered sunlight, e.g., as near a neutral color as possible given the colors of the activated photochromic materials, and an increased level of ultraviolet radiation absorption. In one embodiment, the photochromic materials could be used to produce articles having a wide range of colors, e.g., pink. Further discussion of neutral colors and ways to describe colors can be found in U.S. Pat. No. 5,645,767 column 12, line 66 to column 13, line 19.

The amount of photochromic material (b) to be incorporated into or applied to an organic polymeric material of the photochromic ocular device of the present invention can vary widely. Generally, a sufficient amount is used to produce the desired level of ultraviolet absorption. Such an amount can be described as an ultraviolet radiation absorbing amount. The particular amount used often depends upon the desired level of ultraviolet radiation absorption and the expected intensity of the ultraviolet radiation exposure. Typically, the more photochromic material (b) applied or incorporated, the greater is the amount of ultraviolet radiation absorbed up to a certain limit. There is a point after which the addition of any more material will not have a noticeable effect, although it can be added, if desired.

The amount of photochromic material (b) to be incorporated by addition and/or imbibition into the materials used to produce the organic polymeric material can range from 0.01 to 10.0 weight percent, based on the total weight of the organic polymeric material. Alternate embodiments include from 0.1 to 5 weight percent, from 0.5 to 5.0 weight percent, from 1 to 3 weight percent or from 1.5 to 2.5 weight percent. The amount of photochromic material (b) resulting in the organic polymeric material can range between any combination of these values, inclusive of the recited range, e.g., 0.011 to 9.99 weight percent.

The amount of photochromic materials (c) to be incorporated into an organic polymeric material can also vary widely. Generally, a sufficient amount is used with photochromic material (b) to produce a photochromic effect discernible to the naked eye upon activation. Such amount can be described as a photochromic amount. The particular amount used depends often upon the intensity of color desired upon irradiation thereof and upon the method used to incorporate the photochromic materials. Typically, the more photochromic incorporated, the greater is the color intensity up to a certain limit. There is a point after which the addition of any more material will not have a noticeable effect, although it can be added, if desired.

The relative amounts of the aforesaid photochromic materials (b) or combinations thereof with photochromic materials (c) used may vary and depend in part upon the relative intensities of the color of the activated species of such materials, the ultimate color desired, the amount of ultraviolet radiation to be absorbed and the method of application to the organic polymeric material. In one embodiment, the amount of total photochromic material which includes photochromic material (b), photochromic materials (c) or both, incorporated by imbibition or addition to the materials used to produce the organic polymeric material is the same as stated hereinabove for photochromic material (b).

In one embodiment, compatible (chemically and colorwise) tints, e.g., dyes, can be added or applied to the organic polymeric material used to produce the photochromic ocular device to achieve a more aesthetic result, for medical reasons, or for reasons of fashion. The particular dye selected will vary and depend on the aforesaid need and result to be achieved. The dye can be selected to complement the color resulting from the activated photochromic materials, e.g., to achieve a more neutral color or absorb a particular wavelength of incident light. The dye can also be selected to provide a desired hue to the host material when the photochromic materials are in an unactivated state.

In various embodiments, adjuvant materials can also be incorporated into host material used to produce the photochromic article. Such adjuvants can be used, prior to, simultaneously with or subsequent to application or incorporation of the photochromic material. For example, other ultraviolet light absorbing materials discussed hereinafter can be admixed and/or reacted with photochromic materials before their addition to the composition to enhance ultraviolet radiation absorption and/or improve the light fatigue resistance of the photochromic materials. Examples of stabilizers include hindered amine light stabilizers (HALS), asymmetric diaryloxalamide (oxanilide) compounds and singlet oxygen quenchers, e.g., a nickel ion complex with an organic ligand, polyphenolic antioxidants or mixtures of such stabilizers are contemplated. In one embodiment, they can be used alone or in combination. Such stabilizers are known to those skilled in the art and are described in U.S. Pat. Nos. 4,720,356, 5,391,327 and 5,770,115.

In the context of the present invention, the exact nature of the organic polymeric material is not important and a wide variety of materials can be used. Generally, materials are selected that permit the reversible transformation of photochromic material (b) with or without photochromic material (c) between their "open" and "closed" forms. In one embodiment, the organic polymer composition used to produce the photochromic ocular devices of the present invention comprises compositions adapted to provide thermoplastic or thermosetting organic polymeric materials that are known in the art and are described in the *Kirk-Othmer Encyclopedia of Chemical Technology*, Fourth Edition, Volume 6, pages 669 to 760. Such organic polymeric materials can be transparent, translucent or opaque; but desirably are transparent.

A wide variety of polymerizable monomers can be used to produce the organic polymeric material of the present invention. In one embodiment, the organic polymeric material is polymerized from monomers selected from hydroxyethyl methacrylate, N-vinyl pyrrolidone, methacrylic acid, methyl methacrylate, styrene, alpha-methylstyrene, vinyltoluene, p-chlorostyrene, o-chlorostyrene, p-bromostyrene, o-bromostyrene, divinylbenzene, divinylbiphenyl, vinyl acetate, vinyl propionate, vinyl benzoate, ethyl(meth)acrylate, isopropyl(meth)acrylate, allyl(meth)acrylate, phenyl(meth)acrylate, benzyl(meth)acrylate, p-chlorophenyl(meth)acrylate, p-chlorobenzyl(meth)acrylate, p-bromophenyl(meth)acrylate, p-bromobenzyl(meth)acrylate, naphthyl(meth)acrylate, (meth)acrylamide, N,N-dimethyl(meth)acrylamide, N,N-diethyl(meth)acrylamide, 2-hydroxy-3-phenoxypropyl(meth)acrylate, ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, glycerol di(meth)acrylate, 3-acryloyloxyglycerol monomethacrylate, trimethylolpropane tri(meth)acrylate, pentaerythritol tetra(meth)acrylate, 2,2-bis(4-(meth) acryloyloxy(2'-hydroxypropyloxy)phenyl)propane, diisopropyl fumarate, diisopropyl maleate, dibenzyl fumarate, dibenzyl maleate, dibenzyl mesaconate, maleic anhydride, and itaconic anhydride. These monomers can be used alone or in mixtures thereof.

In a further embodiment, the monomers used to produce the organic polymeric material include monomers used to produce hydrogel polymers. A hydrogel is a crosslinked polymeric system that can absorb and retain water in an equilibrium state. Hydrogel polymers can be formed by polymerizing at least one hydrophilic monomer and at least one crosslinking agent (a crosslinking agent being defined herein as a monomer having multiple polymerizable functionalities). Representative hydrophilic monomers include: unsaturated carboxylic acids, such as methacrylic acid and acrylic acid; (meth)acrylic substituted alcohols, such as 2-hydroxyethylmethacrylate and 2-hydroxyethylacrylate; vinyl lactams, such as N-vinyl pyrrolidone; and (meth)acrylamides, such as methacrylamide and N,N-dimethylacrylamide. Examples of crosslinking agents include polyvinyl, typically di- or tri-vinyl monomers, such as di- or tri(meth)acrylates of diethyleneglycol, triethyleneglycol, butyleneglycol and hexane-1,6-diol; and divinylbenzene. A specific example of a hydrogel polymer-forming monomer mixture is composed primarily of 2-hydroxyethylmethacrylate with a small amount of diethyleneglycol dimethacrylate as a crosslinking monomer.

In a still further embodiment, the polymerizable monomer mixture can optionally include a silicone-containing monomer in order to form a silicone hydrogel polymer. A silicone-containing monomer is one that contains at least one [—Si—O—] group in a monomer, macromer or prepolymer. Examples of silicone-containing monomers include: monomers including a single activated unsaturated radical, such as methacryloxypropyl tris(trimethylsiloxy)silane, pentamethyldisiloxanyl methylmethacrylate, tris(trimethylsiloxy)-methacryloxypropylsilane, methyldi(trimethylsiloxy)-methacryloxymethylsilane, 3-[tris(trimethylsiloxy)silyl]propyl vinylcarbamate, and 3-[tris(trimethylsiloxy)silyl]propylvinyl carbonate; and multifunctional ethylenically "end-capped" siloxane-containing monomers, e.g., difunctional monomers having two activated unsaturated radicals. A specific example of a silicone hydrogel polymer-forming monomer mixture is balafilcon, based on N-vinyl pyrrolidone and the aforementioned vinyl carbonate and carbamate monomers, disclosed in U.S. Pat. No. 5,260,000. Examples of silicone-containing monomers are disclosed in U.S. Pat. No. 6,020,445 at column 4, line 48 to column 8, line 45, which disclosure is incorporated herein by reference. Many other lens-forming monomers and specific mixtures thereof are well known in the art, e.g., monomers disclosed in U.S. Pat. No. 5,637,726 at column 3, line 40 to column 4, line 8.

In another embodiment, ultraviolet radiation absorbing materials can be used to enhance the reduction in ultraviolet radiation by photochromic material (b). Such materials include ultraviolet absorbing monomers. Examples of such materials include: benzotriazole (meth)acrylate esters, e.g., 2-[2'-hydroxy-5'-acryloyloxyalkylphenyl]-2H-benzotriazoles, 2-[2'-hydroxy-5'-acryloyloxy-alkoxyphenyl]-2H-benzotriazoles, and 2-(2'-hydroxyphenyl)-5(6)-(acryloylalkoxy)benzotriazoles.

Examples of benzotriazole UV-absorbing (meth)acrylate esters that can be used in the invention include the following materials: 2-(2'-hydroxy-5'-methacryloxyethyl-phenyl)-2H-benzotriazole; 2-(2'-hydroxy-5'-methacryloxyethyl-phenyl)-5-chloro-2H-benzotriazole; 2-(2'-hydroxy-5'-methacryloxy-propylphenyl)-5-chloro-2H-benzotriazole; 2-(2'-hydroxy-5'-methacryloxypropyl-3'-tert-butylphenyl)-2H-benzotriazole; 2-(2'-hydroxy-5'-methacryloxypropyl-3'-tert-butylphenyl)-5-chloro-2H-benzotriazole; 2-[2'-hydroxy-5'-(2-methacryloyloxyethoxy)-3'-tert-butylphenyl]-5-methoxy-2H-benzotriazole; 2-[2'-hydroxy-5'-(gamma-methacryloyloxypropoxy)-3'-tert-butylphenyl]-5-methoxy-2H-benzotriazole; 2-(3'-t-butyl-2'-hydroxy-5'-methoxyphenyl)-5-(3'-methacryloyloxypropoxy)benzotriazole or mixtures thereof.

In another embodiment of the present invention, photochromic materials (b) can be used in conjunction with a reduced level of the aforementioned non-photochromic UV absorbing materials to produce a photochromic ocular device that meets recommended guidelines for the transmission of ultraviolet radiation through such devices.

A general method for incorporating photochromic materials into ocular devices, e.g., hydrophilic contact lenses, is disclosed in U.S. Pat. No. 6,224,945 B1 at column 5 lines 1 to 47, which disclosure is incorporated herein by reference. In that method, an impregnating solution is used which has a concentration of photochromic material generally from 0.0001 to 1 percent by weight in one embodiment. In an alternate embodiment, the impregnating solution can have a concentration of from 0.05 to 0.25 percent by weight.

The impregnating of the contact lens material is generally carried out by immersion, at room temperature, of the polymeric material in the photochromic solution with stirring. The duration of immersion varies according to the nature of the polymeric material and of the photochromic solution and it typically takes about 5 minutes.

After impregnating, the polymeric material is treated with an aqueous solution, e.g., physiological saline, in order to replace the impregnated solvent with the aqueous solution.

In an alternative embodiment, photochromic material (b) with or without photochromic material (c) can be incorporated into ocular devices, e.g., hydrophilic contact lenses, using mold casting techniques. The mold casting technique comprises the direct molding of a monomer mixture wherein the mixture including the photochromic material is dissolved in a non-aqueous, water-displaceable solvent. The resulting mixture is placed in a mold having the shape of the final desired photochromic ocular device, and subjected to conditions whereby the monomer(s) polymerize, to thereby produce a polymerizate in the shape of the final desired photochromic ocular device.

Polymerization is typically carried out in a substantially non-aqueous medium because water can inhibit the polymerization reaction. After the polymerization is complete, the solvent is displaced with water to produce a hydrated lens whose final size and shape are quite similar to the size and shape of the original casting mold. A direct molding process of hydrogel contact lenses is disclosed in U.S. Pat. No. 4,495,313 at column 2, line 43 to column 6, line 56, and in U.S. Pat. No. 4,680,336 at column 4 line 45 to column 12 line 5, which disclosures are incorporated herein by reference.

The present invention is more particularly described in the following Example and Comparative Example, which are intended as illustrative only, since numerous modifications and variations therein will be apparent to those skilled in the art.

EXAMPLE

The Ultraviolet Photochromic Performance Test was conducted on the lens by measuring the activated and unactivated spectra over a wavelength range of from 300 to 700 nm and determining the ratio of increased ultraviolet radiation absorbance to increased visible radiation absorbance as described hereinbelow.

A hydrophilic contact lens composed of methylmethacrylate and N-vinylpyrrolidone in a 28:72 weight ratio, which composition is equivalent to that of the Rythmic® contact lens available from Essilor International, except that it did not contain a UV absorber, was used. The lens, in the hydrated state, was immersed in a vessel containing 2 milliliters (mL) of dimethyl sulfoxide (DMSO) solution having 0.05 weight percent of 3-(4-methoxyphenyl)-3-phenyl-6,11-dimethoxy-13-methyl-13-(2-(2-hydroxyethyl)ethoxy)-3H,13H-indeno [2,'3,'3,4]-naphtho-[1,2-b]pyran. The aforementioned weight percent is based on the total weight of the solution. The immersed lens was stirred for a period of 5 minutes at room temperature. Afterwards, the lens was rinsed with physiological saline and immersed in physiological saline until the initial diameter was recovered (approximately ten minutes). The resulting lens was steam sterilized at 121° C. for 20 minutes.

After cooling to room temperature, the hydrated lens was placed in a quartz Special Cell measuring 30 mm by 22 mm by 3 mm, made by Starna Cells, Inc., containing physiological saline. The Special Cell was then placed in a carrier suitable for use in a Cary Ultraviolet/Visible spectrophotometer Model #4000. An Ultraviolet-Visible absorption spectrum was collected before exposure to UV and after the lens was exposed to enough UV radiation to lower the visible light transmittance to of 30 percent through the lens. This was accomplished by exposing the lens in the holder to radiation from a Spectroline Long-Wavelength (365 nm) lamp for 15 to 20 seconds.

The resulting spectra were analyzed and the ratio of increased ultraviolet absorbance and increased visible absorbance were determined by measuring the greatest difference in absorbance between the unactivated and activated spectra lines in the ultraviolet range of from 300 to 400 nanometers and dividing that number by the greatest difference between the unactivated and activated spectra lines in the visible range of from 400 to 700 nanometers. The spectrum for the Example of the present invention is shown in FIG. 1. The greatest difference in absorbance in the ultraviolet spectrum is 28 millimeters (mm) at 385 nm and the greatest difference in the visible spectrum is 30 mm at 575 nm. The resulting ratio is 0.93:1.0.

COMPARATIVE EXAMPLE

The procedure of the Example was followed except that Photochromic compound (I) from U.S. Pat. No. 6,224,945 B1, which is reported to be 3,3-di(4-methoxyphenyl)-6,11-dimethyl-13-methyl-13-hydroxy-indeno[2,'3,'3,4]naphtho [1,2-b]pyran, was used. The spectrum of the Comparative Example is shown in FIG. 2. The greatest difference in absorbance in the ultraviolet spectrum is 13 millimeters (mm) at 315 nm and the greatest difference in the visible spectrum is 31 mm at 555 nm. The resulting ratio is 0.42:1.0.

From the spectra presented in FIG. 1, it is apparent that upon activation, the lens develops absorbance not only in the visible portion of the spectrum (providing protection from glare), but also in the ultraviolet portion of the spectrum.

An estimate of the increase in absorbance can be made directly from the graph in absorbance units instead of by measuring the distance between the lines as done hereinabove. The increase in absorbance at 385 nm (1.0−0.5=0.5) is nearly equivalent to the absorbance at 575 nm (absorbance=0.5). Therefore the ratio in the Ultraviolet Photochromic Performance Test is 1.0:1.0.

From the spectra presented in FIG. 2, the increase in absorbance at 315 nm is 0.2 and the increase in absorbance at 555 nm is 0.4. The resulting ratio in the Ultraviolet Photochromic Performance Test is 0.5:1.0.

While the present invention has been described with respect to particular embodiments of apparatus, methods and materials, it will be appreciated that various modifications and adaptations can be made based on the present disclosure and are intended to be within the scope of the accompanying claims.

I claim:

1. A photochromic ocular device selected from a contact lens and an intraocular device, comprising:
   (A) an organic polymeric material; and
   (B) at least one organic photochromic material able to change from a less radiation absorbing unactivated form to a more radiation absorbing activated form upon exposure to actinic radiation;

wherein said photochromic ocular device upon exposure to actinic radiation exhibits a ratio of increased ultraviolet radiation absorbance to increased visible radiation absorbance of greater than 0.5:1.0 as measured in the Ultraviolet Photochromic Performance Test, and wherein the photochromic material of (B) is represented by Structure II:

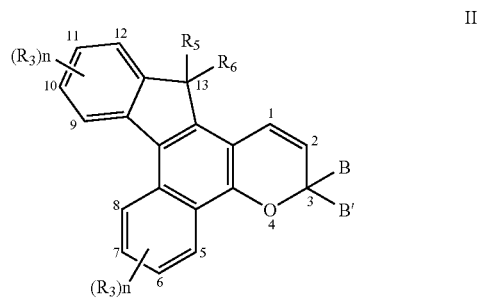

wherein,
  (a) R is a group which is represented by one of the following formulae:

—A                               (formula IVA);

—D—A                             (formula IVB);

—D—E—U                           (formula IVC);

—D—U                             (formula IVD);

—E—U                             (formula IVE); or

—U                               (formula IVF);

wherein —A is represented by the following formula:

—[(OC$_2$H$_4$)$_x$(OC$_3$H$_6$)$_y$(OC$_4$H$_8$)$_z$]—J wherein —J is selected from: hydroxy; (meth)acryloxy; 2-(methacryloxy)ethylcarbamyl; epoxy; —OCH$_2$COOH; —OCH(CH$_3$)COOH; —OC(O) (CH$_2$)$_w$ COOH; —OC$_6$H$_4$SO$_3$H; —OC$_5$H$_{10}$SO$_3$H; —OC$_4$H$_8$SO$_3$H; —OC$_3$H$_6$SO$_3$H; —OC$_2$H$_4$SO$_3$H; and —OSO$_3$H; w is an integer from 1 to 18; x, y and z are each a number between 0 and 50, and the sum of x, y and z is between 1 and 50; —D— is —C(O)— or —CH$_2$—; —E— is represented by the following formula:

—[(OC$_2$H$_4$)$_x$(OC$_3$H$_6$)$_y$(OC$_4$H$_8$)$_z$]— wherein x, y and z are the same as defined for —A; —U is a residue of an organic polyol having at least one hydroxyl group or a derivative of said residue, wherein at least one hydroxyl group has been reacted to form the group J provided that —U is not the same as —A when —J is hydroxy;

(b)
at least one $R_3$ group in Structure II is attached at each of positions 6 and 11, each $R_3$ is independently selected from the group R wherein R is —A, —EU, or —U, phenyl, mono-substituted phenyl, di-substituted phenyl, and the group —$OR_{10}$, wherein $R_{10}$ is $C_1$-$C_6$ alkyl, phenyl($C_1$-$C_3$)-alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, $C_1$-$C_6$ alkoxy($C_2$-$C_4$)alkyl, $C_3$-$C_7$ cycloalkyl or mono($C_1$-$C_4$)alkyl substituted $C_3$-$C_7$ cycloalkyl, the phenyl substituent being $C_1$-$C_6$ alkyl or $C_1$-$C_6$ alkoxy; or each $R_3$ is independently a nitrogen-containing group selected from:
  (i) —N($R_{11}$)$R_{12}$ wherein $R_{11}$ and $R_{12}$ are each independently selected from hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl and $C_1$-$C_{20}$ alkoxyalkyl, wherein the aryl group is phenyl or naphthyl or $R_{11}$ and $R_{12}$ come together with the nitrogen atom to form a $C_3$-$C_{20}$ hetero-bicycloalkyl ring or a $C_4$-$C_{20}$ hetero-tricycloalkyl ring;
  (ii) a nitrogen containing ring represented by the following graphic formula VA:

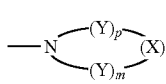

VA wherein each Y is independently selected for each occurrence from —$CH_2$—, —CH($R_{13}$)—, —C($R_{13}$)($R_{13}$)—, —CH(aryl)-, —C(aryl)$_2$-, and —C($R_{13}$)(aryl)-, and X is selected from —Y—, —O—, —S—, —S(O)—, —S($O_2$)—, —NH—, —N($R_{13}$)— and —N(aryl)-, wherein $R_{13}$ is $C_1$-$C_6$ alkyl, said aryl is phenyl or naphthyl, m is the integer 1, 2 or 3, and p is the integer 0, 1, 2, or 3 and when p is O, X is Y;
  (iii) a group represented by one of the following graphic formulae VB and VC:

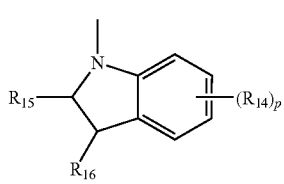

VB

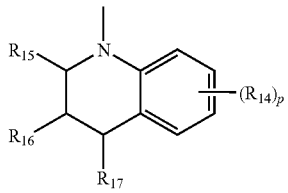

VC wherein $R_{15}$, $R_{16}$ and $R_{17}$ are each independently selected for each occurrence in each formula from hydrogen, $C_1$-$C_6$ alkyl, phenyl and naphthyl, or the groups $R_{15}$ and $R_{16}$ together form a ring of 5 to 8 carbon atoms and each $R_{14}$ is independently selected for each occurrence in each formula from $C_1$-$C_6$ alkyl, $C_1$-$C_6$ alkoxy, fluoro and chloro and p is the same as defined above;
  (iv) unsubstituted, mono- or di-substituted $C_4$-$C_{18}$ spirobicyclic amine; and
  (v) unsubstituted, mono- or di-substituted $C_4$-$C_{18}$ spirotricyclic amine; wherein substituents for (b) (iv) and (v) are independently selected for each occurrence from aryl, $C_1$-$C_6$ alkyl, $C_1$-$C_6$ alkoxy and phenyl($C_1$-$C_6$)alkyl and n is selected from the integers 0, 1 and 2;
(c) $R_5$ and $R_6$ together form an oxo group, a spiro-carbocyclic ring containing 3 to 6 carbon atoms or a spiro-heterocyclic group containing 1 or 2 oxygen atoms and 3 to 6 carbon atoms including the spirocarbon atom, said spiro-carbocyclic and spiro-heterocyclic groups being annellated with 0, 1 or 2 benzene rings; or $R_5$ and $R_6$ are each independently the group R, hydrogen, $C_1$-$C_6$ alkyl, $C_3$-$C_7$ cycloalkyl, allyl, phenyl, mono-substituted phenyl, benzyl, mono-substituted benzyl, chloro, fluoro, the group, —C(O)X', wherein X' is hydroxy, $C_1$-$C_6$ alkyl, $C_1$-$C_6$ alkoxy, phenyl, mono-substituted phenyl, amino, mono($C_1$-$C_6$)alkylamino, or di($C_1$-$C_6$)alkylamino; or $R_5$ and $R_6$ are each independently the group, —$OR_{18}$, wherein $R_{18}$ is $C_1$-$C_6$ alkyl, phenyl($C_1$-$C_3$)alkyl, mono($C_1$-$C_6$) alkyl substituted phenyl($C_1$-$C_3$)alkyl, mono($C_1$-$C_6$) alkoxy substituted phenyl($C_1$-$C_3$)alkyl, $C_1$-$C_6$ alkoxy ($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, the group, —CH($R_{19}$)Y', wherein $R_{19}$ is hydrogen or $C_1$-$C_3$ alkyl and Y' is CN, $CF_3$, or $COOR_{20}$ and $R_{20}$ is hydrogen or $C_1$-$C_3$ alkyl; or $R_{18}$ is the group, —C(O)Z, wherein Z is hydrogen, $C_1$-$C_6$ alkyl, $C_1$-$C_6$ alkoxy, the unsubstituted, mono- or di-substituted aryl groups phenyl or naphthyl, phenoxy, mono- or di-($C_1$-$C_6$)alkyl substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, each of said phenyl, benzyl and aryl group substituents being $C_1$-$C_6$ alkyl or $C_1$-$C_6$ alkoxy;
(d) B is selected from the unsubstituted aryl groups, phenyl and naphthyl; and
(e) B' is selected from:
  (i) the unsubstituted, mono-, di- or tri-substituted aryl groups, phenyl and naphthyl;
  (ii) 9-julolidinyl or the unsubstituted, mono- or di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl or fluorenyl, each of said aryl and heteroaromatic substituents in (e)(i) and (ii) being selected from the group R, $C_1$-$C_6$ alkyl, $C_1$-$C_6$ chloroalkyl, $C_1$-$C_6$ fluoroalkyl, $C_1$-$C_6$ alkoxy, mono($C_1$-$C_6$)alkoxy($C_1$-$C_4$)alkyl, acryloxy, methacryloxy, bromo, chloro, fluoro, aryl, mono($C_1$-$C_6$)alkoxyaryl, di($C_1$-$C_6$)alkoxyaryl, mono($C_1$-$C_6$)alkylaryl, di($C_1$-$C_6$)alkylaryl, chloroaryl, fluoroaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_6$)alkyl, $C_3$-$C_7$ cycloalkyloxy($C_1$-$C_6$) alkoxy, aryl($C_1$-$C_6$)alkyl, aryl($C_1$-$C_6$)alkoxy, aryloxy, aryloxy($C_1$-$C_6$)alkyl, aryloxy($C_1$-$C_6$)alkoxy, mono- or di-($C_1$-$C_6$)alkylaryl($C_1$-$C_6$)alkyl, mono- or di-($C_1$-$C_6$)alkoxyaryl($C_1$-$C_6$)alkyl, mono- or di-($C_1$-$C_6$)alkylaryl($C_1$-$C_6$)alkoxy, mono- or di-($C_1$-$C_6$)alkoxyaryl($C_1$-$C_6$)alkoxy, said aryl being phenyl or naphthyl;

(iii) monosubstituted phenyl, having at the para position a substituent that is —($CH_2$)$_t$— or —O—($CH_2$)$_t$—, wherein t is the integer 1, 2, 3, 4, 5 or 6, said substituent being connected to an aryl group on another photochromic material;

(iv) the group represented by one of the following graphic formulae VIA or VIB:

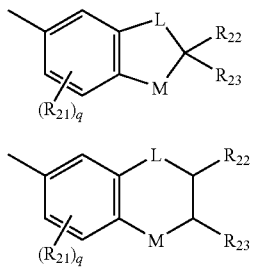

wherein L is carbon or oxygen and M is oxygen; each $R_{21}$ is $C_1$-$C_6$ alkyl, $C_1$-$C_6$ alkoxy, hydroxy, chloro or fluoro; $R_{22}$ and $R_{23}$ are each hydrogen or $C_1$-$C_6$ alkyl; and q is the integer 0, 1 or 2; and (v) the group represented by the following graphic formula VIC:

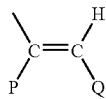

wherein P is hydrogen or $C_1$-$C_4$ alkyl and Q is an unsubstituted, mono- or di-substituted group, said group being selected from naphthyl, phenyl, furanyl and thienyl, each of said group substituents being $C_1$-$C_4$ alkyl, $C_1$-$C_4$ alkoxy, fluoro or chloro; provided that there is at least one R group or mono-R-substituted phenyl as a substituent on the photochromic material of (B) and if the mono-R-substituted phenyl group is B' said R group is one of formula IVA to IVF provided that —J of —A in formula IVA and IVB is not hydroxy, (meth)acryloxy or epoxy.

2. The photochromic ocular device of claim 1 wherein the photochromic materials of (B) are represented by Structure II wherein:

(a)
each $R_3$ independently comprises the group R represented by formula: (IVA); (IVE); or (IVF) or the group —OR$_{10}$, wherein $R_{10}$ is $C_1$-$C_4$ alkyl, phenyl($C_1$-$C_2$)alkyl, mono($C_1$-$C_4$)alkyl substituted phenyl($C_1$-$C_2$)alkyl, mono($C_1$-$C_4$)alkoxy substituted phenyl($C_1$-$C_2$)alkyl, $C_1$-$C_4$ alkoxy($C_2$-$C_4$)alkyl, $C_5$-$C_7$ cycloalkyl or mono($C_1$-$C_3$) alkyl substituted $C_5$-$C_7$ cycloalkyl and said phenyl substituents being $C_1$-$C_3$ alkyl or $C_1$-$C_3$ alkoxy; or each $R_3$ is independently a nitrogen-containing group selected from:

(i) —N($R_{11}$)$R_{12}$, $R_{11}$ and $R_{12}$ each being independently selected from $C_1$-$C_6$ alkyl and phenyl;

(ii) a nitrogen-containing ring represented by the graphic formula VA wherein each Y is —$CH_2$— and X is independently selected from —Y—, —O—, —S—, —N($R_{13}$)— and —N(phenyl)-, $R_{13}$ being $C_1$-$C_6$ alkyl, m being selected from the integers 1, 2 and 3, and p selected from the integers 0, 1, 2 and 3;

(iii) a group represented by one of graphic formulae VB and VC wherein $R_{15}$, $R_{16}$ and $R_{17}$ each are independently selected from hydrogen and $C_1$-$C_5$ alkyl, $R_{14}$ is independently selected from hydrogen, $C_1$-$C_4$ alkyl, $C_{1-4}$ alkoxy, fluoro and chloro;

(iv) unsubstituted or mono-substituted $C_5$-$C_{18}$ spirobicyclic amine; and (v) unsubstituted or mono-substituted $C_5$-$C_{18}$ spirotricyclic amine; the substituents for (a)(iv) and (v) independently selected for each occurrence from phenyl, $C_1$-$C_6$ alkyl and $C_1$-$C_6$ alkoxy and n selected from the integers 1 and 2;

(b) $R_5$ and $R_6$ are each independently selected from the group R, hydrogen, $C_1$-$C_4$ alkyl, $C_3$-$C_6$ cycloalkyl, chloro, fluoro and the group, —OR$_{18}$, wherein $R_{18}$ is $C_1$-$C_3$ alkyl, phenyl($C_1$-$C_2$)alkyl, mono($C_1$-$C_3$)alkyl substituted phenyl($C_1$-$C_3$)alkyl, mono($C_1$-$C_3$)alkoxy substituted phenyl($C_1$-$C_3$)alkyl, $C_1$-$C_3$ alkoxy($C_2$-$C_4$) alkyl, $C_1$-$C_3$ chloroalkyl, $C_1$-$C_3$ fluoroalkyl, the group, —CH($R_{19}$)Y', wherein $R_{19}$ is hydrogen or $C_1$-$C_2$ alkyl and Y' is CN or COOR$_{20}$, and $R_{20}$ is hydrogen or $C_1$-$C_2$ alkyl, or $R_{18}$ is the group, —C(O)Z, wherein Z is hydrogen, $C_1$-$C_3$ alkyl, $C_1$-$C_3$ alkoxy, phenyl, naphthyl, mono-substituted aryl groups, phenyl or naphthyl, phenoxy, mono- or di-($C_1$-$C_3$)alkyl substituted phenoxy, mono- or di-($C_1$-$C_3$)alkoxy substituted phenoxy, mono ($C_1$-$C_3$)alkylamino, phenylamino, mono- or di-($C_1$-$C_3$) alkyl substituted phenylamino, or mono- or di-($C_1$-$C_3$) alkoxy substituted phenylamino, and said aryl substituents being $C_1$-$C_3$ alkyl or $C_1$-$C_3$ alkoxy;

(c) B is phenyl; and (d) B' is selected from:
(i) phenyl, mono-substituted or di-substituted phenyl, each of said phenyl substituents being independently selected from the group R, awl, aryloxy, aryl($C_1$-$C_3$) alkyl, $C_1$-$C_3$ alkyl, $C_1$-$C_3$ chloroalkyl, $C_1$-$C_3$ fluoroalkyl, $C_1$-$C_3$ alkoxy, mono($C_1$-$C_3$)alkoxy($C_1$-$C_3$) alkyl, chloro and fluoro;

(ii) the groups represented by one of graphic formulae VIA and VIB: wherein L is carbon and M is oxygen, $R_{21}$ is $C_1$-$C_3$ alkyl or $C_1$-$C_3$ alkoxy; $R_{22}$ and $R_{23}$ are each hydrogen or $C_1$-$C_4$ alkyl; and q is 0 or 1; and (iii) the group represented by graphic formula VIC wherein P is hydrogen or methyl and Q is phenyl or mono-substituted phenyl, said phenyl substituents being $C_1$-$C_3$ alkyl, $C_1$-$C_3$ alkoxy or fluoro.

3. The photochromic ocular device of claim 2 wherein the photochromic material of (B) is represented by Structure II wherein:

(a) each $R_3$ is the group R represented by formula (IVE) or (IVF), or the group, OR$_{10}$, wherein $R_{10}$ is $C_1$-$C_3$ alkyl; or each $R_3$ is selected from:

(i) —N($R_{11}$)$R_{12}$, $R_{11}$ and $R_{12}$ each independently being $C_1$-$C_3$ alkyl;

(ii) a nitrogen-containing ring represented by graphic formula VA wherein each Y for each occurrence is —$CH_2$— and X is independently selected from —Y—, —O—, and —N($R_{13}$)—, $R_{13}$ being $C_1$-$C_4$ alkyl, m being selected from the integers 1 and 2, and p being selected from the integers 0, 1 and 2; and (iii) a group represented by graphic formula VC or VB wherein $R_{15}$, $R_{16}$, and $R_{17}$ each independently comprise hydrogen and n is 1 or 2;

(b) $R_5$ and $R_6$ are each independently the group R, hydrogen, $C_1$-$C_4$ alkyl, or the group, —$OR_{18}$, wherein $R_{18}$ is $C_1$-$C_3$ alkyl;

(c) B is phenyl; and (d) B' is selected from phenyl, mono- and di-substituted phenyl, each of the phenyl substituents being selected from the group R, $C_1$-$C_3$ alkyl, $C_1$-$C_3$ alkoxy, phenyl, fluoro and chloro.

4. The photochromic ocular device of claim 2 wherein the photochromic material of (B) is selected from:

(a) 3-(4-methoxyphenyl)-3-phenyl-6,11-dimethoxy-13-methyl-13-(2-{2-[N-(2-methacryloxyethyl)carbamoyloxy]ethoxy}ethoxy)-3H,13H-indeno[2,'3,'3,4]naphtho[1,2-b]pyran;

(b) 3-(4-methoxyphenyl)-3-phenyl-6,11-dimethoxy-13-methyl-13-(2-(2-(2-methacryloxyethyl)ethoxy)ethoxy)-3H,13H-indeno[2,'3,'3,4]naphtho[1,2-b]pyran;

(c) 3,3-diphenyl-6,7-dimethoxy-13-methyl-13-(2-(2-(2-methacryloxyethyl)ethoxy)ethoxy)-3H,13H-indeno[2,'3,'3,4]naphtho[1,2-b]pyran;

(d) 3-(4-methoxyphenyl)-3-phenyl-6-methoxy-7-morpholino-13-methyl-13-(2-(2-(2-methacryloxyethyl)ethoxy)ethoxy)-3H,13H-indeno[2,'3,'3,4]naphtho[1,2-b]pyran;

(e) 3,3-diphenyl-6,7,10,11-tetramethoxy-13-ethyl-13-(2-{2-[N-(2-methacryloxyethyl)carbamoyloxy]ethoxy}ethoxy)-3H,13H-indeno[2,'3,'3,4]naphtho[1,2-b]pyran;

(f) 3-(4-methoxyphenyl)-3-phenyl-6,11-dimethoxy-13-methyl-13-(2-(2-hydroxyethyl)ethoxy)-3H,13H-indeno[2,'3,'3,4]-naphtho-[1,2-b]pyran; and (i) mixtures thereof.

5. The photochromic ocular device of claim 1 wherein the photochromic material of (B) is selected from:

(a) a single photochromic compound;

(b) a mixture of photochromic compounds;

(c) a material comprising at least one photochromic compound;

(d) a material to which at least one photochromic compound is chemically bonded;

(e) material (c) or (d) comprising a coating to substantially prevent contact of the photochromic compound with external materials;

(f) a photochromic polymer; and (g) mixtures thereof.

6. The photochromic ocular device of claim 1 further comprising at least one other photochromic material (c) that is different from the photochromic material of (B).

7. The photochromic ocular device of claim 6 wherein photochromic compound (c) is an organic photochromic compound.

8. The photochromic ocular device of claim 7 wherein photochromic compound (c) is an organic photochromic compound and is selected from chromenes; spiropyrans; oxazines; mercury dithizonates, fulgides, fulgimides or mixtures thereof.

9. The photochromic ocular device of claim 8 wherein the chromene photochromic compound (c) is selected from naphthopyrans, benzopyrans, indenonaphthopyrans, phenanthropyrans and mixtures thereof.

10. The photochromic ocular device of claim 9 wherein the chromene photochromic compound (c) is selected from naphthopyrans, indenonaphthopyrans, and mixtures thereof.

11. The photochromic ocular device of claim 6 wherein photochromic material (c) is selected from:

(a) a single photochromic compound;

(b) a mixture of photochromic compounds;

(c) a material comprising at least one photochromic compound;

(d) a material to which at least one photochromic compound is chemically bonded;

(e) material (c) or (d) comprising a coating to substantially prevent contact of the at least one photochromic compound with external materials;

(f) a photochromic polymer; and (g) mixtures thereof.

12. The photochromic ocular device of claim 1 wherein the organic polymeric material is a polymer prepared from a monomer selected from hydroxyethyl methacrylate, N-vinyl pyrrolidone, methacrylic acid, methyl methacrylate, styrene, alpha-methylstyrene, vinyltoluene, p-chlorostyrene, o-chlorostyrene, p-bromostyrene, o-bromostyrene, divinylbenzene, divinylbiphenyl, vinyl acetate, vinyl propionate, vinyl benzoate, ethyl(meth)acrylate, isopropyl(meth)acrylate, allyl (meth)acrylate, phenyl(meth)acrylate, benzyl(meth)acrylate, p-chlorophenyl(meth)acrylate, p-chlorobenzyl(meth)acrylate, p-bromophenyl(meth)acrylate, p-bromobenzyl(meth)acrylate, naphthyl(meth)acrylate, (meth)acrylamide, N,N-dimethyl(meth)acrylamide, N,N-diethyl(meth)acrylamide, 2-hydroxy-3-phenoxypropyl(meth)acrylate, ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, glycerol di(meth)acrylate, 3-acryloyloxyglycerol monomethacrylate, trimethylolpropane tri(meth)acrylate, pentaerythritol tetra(meth)acrylate, 2,2-bis(4-(meth)acryloyloxy(2'-hydroxypropyloxy)phenyl)propane, diisopropyl fumarate, diisopropyl maleate, dibenzyl fumarate, dibenzyl maleate, dibenzyl mesaconate, maleic anhydride, itaconic anhydride and mixtures thereof.

13. The photochromic ocular device of claim 1 wherein the ratio of increased ultraviolet radiation absorbance to increased visible radiation absorbance as measured in the Ultraviolet Photochromic Performance Test is at least 1.0:1.0.

14. The photochromic ocular device of claim 1 wherein the organic polymeric material is a hydrogel polymer comprising a polymerizate of at least one hydrophilic monomer and at least one crosslinking agent.

15. The photochromic ocular device of claim 14 wherein the at least one hydrophilic monomer is selected from: unsaturated carboxylic acids; (meth)acrylic substituted alcohols; vinyl lactams; (meth)acrylamides; and mixtures thereof.

16. The photochromic ocular device of claim 14 wherein the at least one crosslinking agent is selected from divinylbenzene; di- or tri(meth)acrylates of diethyleneglycol, triethyleneglycol, butyleneglycol or hexane-1,6-diol; and mixtures thereof.

17. The photochromic ocular device of claim 14 wherein the hydrogel polymer further comprises at least one silicone-containing monomer comprising at least one unsaturated group.

18. The photochromic ocular device of claim 17 wherein the at least one silicone-containing monomer is selected from methacryloxypropyl tris(trimethylsiloxy)silane, pentamethyldisiloxanyl methyl methacrylate, tris(trimethylsiloxy)methacryloxy propylsilane, methyldi(trimethylsiloxy)methacryloxymethyl silane, 3-[tris(trimethylsiloxy)silyl]propylvinylcarbamate, and 3-[tris(trimethylsiloxy)silyl]propylvinylcarbonate.

19. The photochromic ocular device of claim 1 further comprising at least one non-photochromic ultraviolet absorbing material.

20. The photochromic ocular device of claim 19 wherein the at least one ultraviolet absorbing material is a monomer selected from: 2-(2'-hydroxy-5'-methacryloxyethyl-phenyl)-2H-benzotriazole; 2-(2'-hydroxy-5'-methacryloxyethyl-phenyl)-6-chloro-2H-benzotriazole; 2-(2'-hydroxy-5'-methacryloxy-propyl phenyl)-5-chloro-2H-benzotriazole; 2-(2'-hydroxy-5'-methacryloxypropyl-3'-tert-butylphenyl)-2H-benzotriazole; 2-(2'-hydroxy-5'-methacryloxypropyl-3'-tert-butyl phenyl)-5-chloro-2H-benzotriazole; 2-[2'-hydroxy-5'-(2-methacryloyloxyethoxy)-3'-tert-butyl phenyl]-5-methoxy-2H-benzotriazole; 2-[2'-hydroxy-5'-(gamma-methacryloyloxypropoxy)-3'-tert-butyl phenyl]-5-methoxy-2H-benzotriazole; 2-(3'-t-butyl-2'-hydroxy-5'-methoxyphenyl)-5-(3'-methacryloyloxypropoxy) benzotriazole and mixtures thereof.

\* \* \* \* \*